(12) United States Patent
Wei et al.

(10) Patent No.: US 10,234,312 B2
(45) Date of Patent: *Mar. 19, 2019

(54) ULTRASONIC WAVE SENSING MODULE

(71) Applicant: Magna Electronics Solutions GmbH, Wetzlar (DE)

(72) Inventors: Jingyuan Wei, Taipei (TW); Jiayu Lin, Taipei (TW)

(73) Assignee: MAGNA ELECTRONICS SOLUTIONS GMBH, Wetzlar (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/914,063

(22) Filed: Mar. 7, 2018

(65) Prior Publication Data

US 2018/0195887 A1 Jul. 12, 2018

Related U.S. Application Data

(63) Continuation of application No. 14/707,552, filed on May 8, 2015, now Pat. No. 9,915,557.

(30) Foreign Application Priority Data

May 8, 2014 (CN) .......................... 2014 1 0191943

(51) Int. Cl.
*G01F 1/66* (2006.01)
*G01N 29/22* (2006.01)
*G01S 15/93* (2006.01)
*G01S 7/521* (2006.01)
*G01S 15/96* (2006.01)

(52) U.S. Cl.
CPC ............ *G01F 1/66* (2013.01); *G01N 29/223* (2013.01); *G01S 7/521* (2013.01); *G01S 15/931* (2013.01); *G01N 2291/101* (2013.01); *G01S 15/96* (2013.01)

(58) Field of Classification Search
CPC .. G01F 1/66; G01N 29/223; G01N 2291/101; G01N 29/22; G01N 29/222; G01N 29/2437; G01N 29/2487; G01S 7/521; G01S 15/931; G01S 15/96; G01D 11/245
USPC ............... 73/632, 641, 649, 866.5; 310/338; 367/140
See application file for complete search history.

(56) References Cited

U.S. PATENT DOCUMENTS 5,767,773 A 6/1998 Fujiuchi et al.
6,862,932 B2 3/2005 Zimmerman et al.
(Continued)

*Primary Examiner* — Lisa M Caputo
*Assistant Examiner* — Suman K Nath
(74) *Attorney, Agent, or Firm* — Honigman LLP

(57) ABSTRACT

A method of forming an ultrasonic wave sensing module for a vehicle includes providing a housing having a first containing space and a second containing space separated from each other by a blocking wall, and providing an adapter at the blocking wall that includes a first connecting portion and a first connecting pin. An ultrasonic wave sensor is disposed in the first containing space and a circuit board is disposed in the second containing space. A second connecting pin of the ultrasonic wave sensor extends into the blocking wall and is coupled to the first connecting portion of the adapter at the blocking wall. A second connecting portion of the circuit board is coupled to the first connecting pin of the adapter. The ultrasonic wave sensor is electrically connected with the circuit board via the adapter.

20 Claims, 3 Drawing Sheets

(56) References Cited

U.S. PATENT DOCUMENTS

| | | |
|---|---|---|
| 9,915,557 B2 * | 3/2018 | Wei .......................... G01F 1/66 |
| 2007/0230273 A1 | 10/2007 | Nakajima et al. |
| 2007/0237031 A1 | 10/2007 | Kawashima et al. |
| 2010/0139389 A1 | 6/2010 | Morita |
| 2012/0243189 A1 | 9/2012 | Urase et al. |
| 2015/0331100 A1 | 11/2015 | Hsu et al. |

* cited by examiner

ULTRASONIC WAVE SENSING MODULE

CROSS-REFERENCE TO RELATED APPLICATIONS

This application is a continuation of U.S. patent application Ser. No. 14/707,552, filed May 8, 2015, now U.S. Pat. No. 9,915,557, which claims the benefit of Chinese Patent Application No. 201410191943.7 filed on May 8, 2014 in the State Intellectual Property Office of China, the disclosure of which is incorporated herein by reference.

FIELD OF THE INVENTION

The present disclosure relates to an ultrasonic wave sensing module, and more particularly, to an ultrasonic wave sensing module for detecting objects.

DESCRIPTION OF THE RELATED ART

Any sonic waves or vibrations having frequency larger than a highest threshold of 20 KHz which can be heard by ears of human being, are called as ultrasonic waves. The ultrasonic wave has been widely applied into many fields, such as radar positioning, medical diagnosis, or distance measurement. Taking the distance measurement as an example, an emitter may be used to emit ultrasonic waves toward a certain direction. The timekeeping is started at the time when ultrasonic waves are emitted. And then, the ultrasonic waves will propagate in the air, and will be reflected back upon colliding with barriers. The timekeeping is stopped once a receiver receives the reflected waves. Thus, a distance of the emitting location from the barrier can be calculated by a traveling speed of the ultrasonic wave and a time length of the timekeeping.

SUMMARY OF THE INVENTION

The present disclosure relates to an ultrasonic wave sensing module, wherein an adapter is used to connect an ultrasonic wave sensor with a circuit board. This simplifies the assembling process and improves the waterproof effect.

In accordance with an embodiment of the present invention, it provides an ultrasonic wave sensing module, including a housing, an ultrasonic wave sensor, an adapter and a circuit board. The housing has a first containing space and a second containing space being separated from each other by a blocking wall. The ultrasonic wave sensor is disposed within the first containing space and has a first connecting pin. The adapter includes a first connecting portion and a second connecting pin, and is integrally formed with the blocking wall by means of insert molding. The circuit board is provided within the second containing space, and has a second connecting portion. The first connecting pin of the ultrasonic wave sensor is coupled to the first connecting portion of the adapter, and the second connecting pin of the adapter is coupled to the second connecting portion of the circuit board, so that the ultrasonic wave sensor and the circuit board are electrically connected.

BRIEF DESCRIPTION OF THE DRAWINGS

In order to better understand the above aspects and other aspects of the present invention, the detailed description is set out therein in conjunction with the specific embodiments with reference to the attached drawings, wherein.

DETAILED DESCRIPTION OF PREFERRED EMBODIMENTS OF THE INVENTION

Embodiments of the present invention will be described in detail with reference to the attached drawings. The same reference numbers in the figures are used to indicate the same or similar parts. It should be noted that the figures are drawn in a simplified way, for sake of clearly illustrating contents of the present embodiments, and dimension scale in the attached figures is not drawn in the same proportion with the practical products, thus it is not intended to limit the scope of the present invention.

Figure 1:
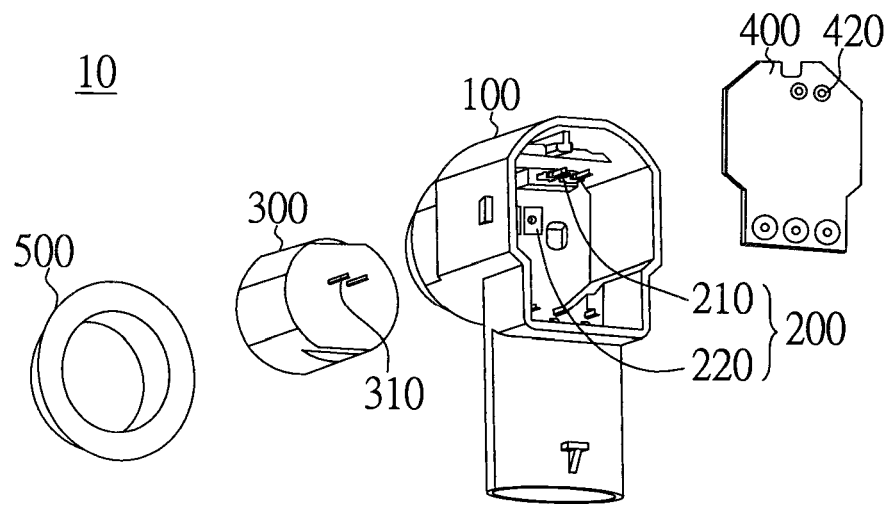
FIG. 1 shows a prospective exploded view of an ultrasonic wave sensing module in accordance with an embodiment of the present invention.

With reference to FIG. 1, it shows a prospective exploded view of an ultrasonic wave sensing module in accordance with an embodiment of the present invention. The ultrasonic wave sensing module 10 is for example a distance sensor, applicable to various prevention devices (for example, car reversing radar of the car) or detection devices (for example, non-destructive inspection, sonar, fish detection), but the present invention is not limited to those. The ultrasonic wave sensing module includes a housing 100, an adapter 200, an ultrasonic wave sensor 300, and a circuit board 400. The housing 100 functions for protection, and is used to accommodate the components such as the adapter 200, the ultrasonic wave sensor 300, and the circuit board 400, in order to prevent foreign matters such as dusts or moisture entering therein. The adapter 200 is used to connect the ultrasonic wave sensor 300 with the circuit board 400. The ultrasonic wave sensor 300 can emit and receive the ultrasonic waves. The circuit board 400 includes various circuit elements (not shown) like driving IC thereon, which can be used to manipulate the ultrasonic wave sensor 300 and process the received signals. In addition, the ultrasonic wave sensing module 10 may also include a rubber pad or ring 500 surrounding the ultrasonic wave sensor 300, so that the ultrasonic wave sensor 300 can be more firmly fixed into the housing 100, the influence of the vibrations to the ultrasonic wave sensor 300 can be reduced, and the risk of moisture or dusts entering the housing 100 can be decreased.

Figure 2:
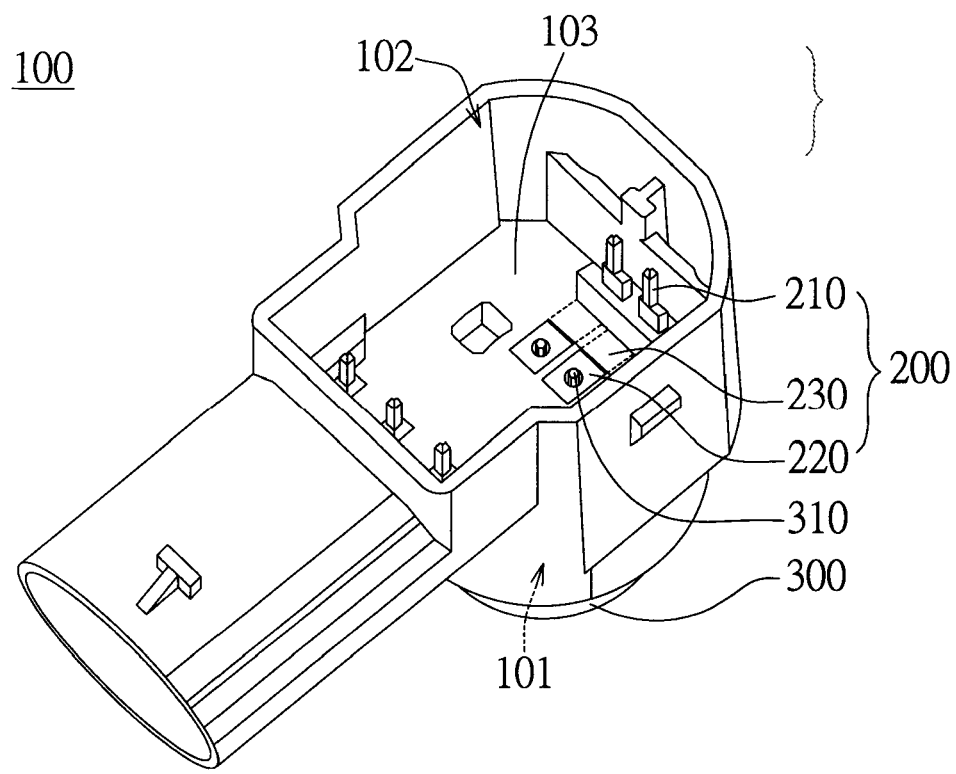
FIG. 2 shows a schematic view of a housing and an ultrasonic wave sensor assembled together, within the ultrasonic wave sensing module as shown in FIG. 1.

With reference to FIG. 2, it shows a schematic view of the assembled housing 100 and ultrasonic wave sensor 300, within the ultrasonic wave sensing module 10 as shown in FIG. 1. The housing 100 has a first containing space 101 and a second containing space 102, which are separated from each other by a blocking wall 103. The first containing space 101 can be used to accommodate the ultrasonic wave sensor 300 and the rubber pad 500 (please see FIG. 1), and the second containing space 102 can be used to accommodate the circuit board 400 (please see FIG. 1). The housing 100 in the present embodiment has a shape like a T-shaped connection pipe. In addition to two arms of the T-shaped connection pipe having the respective containing spaces, the bottom thereof is also provided with an additional containing space, which is configured to connect other elements such as the power supply. However, the present invention does not limit the shape of the housing, and any shapes having two containing spaces for accommodating the ultrasonic wave sensor and the circuit board respectively are feasible for the housing of the present disclosure. The blocking wall 103 separate the first containing space 101 from the second containing space 102, and the adapter 200 located in the blocking wall 103 electrically connects the ultrasonic wave sensor 300 in the first containing space 101 with the circuit board 400 in the second containing space 102.

With reference to FIGS. 1 and 2 together, the adapter 200 is located inside the blocking wall 103, and includes a second connecting pin 210 and a first connecting portion 220. The method of disposing the adapter 200 into the blocking wall 103 is for example an insert molding. The insert molding is a molding technique for plastics. An insert part (the adapter 200 herein) is placed into the mould, and then the plastic is charged into the mould, so that the insert and the coated part (plastic) are integrally formed. Thus, the present disclosure omits secondary manufacturing process such as adhering and assembling processes, compared with the conventional assembling way in which an additional fixing piece is needed to fix the connecting pin. The insert molding method employed by the present embodiment not only shortens the assembling time, but also saves costs of the parts. Furthermore, the manufacturing process of insert molding can reduce opening area of the holes on the blocking wall for the assembling, so that the separation between the first containing space 101 and the second containing space 102 are enhanced, and waterproof and dustproof effects of the housing 110 to the circuit board 400 can be improved.

As shown in FIG. 1, the second connecting pin 210 of the adapter 200 is used to be connected with the second connecting portion 420 of the circuit board 400, whereas the first connecting portion 220 of the adapter 200 is used to be connected with a first connecting pin 310 of the ultrasonic wave sensor 300, so that the ultrasonic wave sensor 300 is electrically connected with the circuit board 400. In the present embodiment, the first connecting pin 310 and the second connecting pin 210 are two needle-shaped connecting pins, and the first and second connecting portions 220 and 420 are jacks. The needle-shaped connecting pins can be inserted into the jacks, and be fixed by the means of welding or the like. It should be especially noted that the present invention does not limit the number and shapes of the connecting portions and the connecting pins. For example, in other embodiments, the connecting portions and the connecting pins can be connecting pads, and are fixed together by contacting, magnetic force or adhesives.

As shown in FIG. 2, the second connecting pin 210 and the first connecting portion 220 of the adapter 200 can be provided at different positions on the blocking wall 103 respectively, and they are electrically connected via an extension portion 230. In this way, the position of the second connecting portion 420 on the circuit board 400 does not necessarily correspond to that of the first connecting pin 310 on the ultrasonic wave sensor 300 (as shown in FIG. 1), so that the circuit design of the circuit board 400 is more flexible.

Figure 3:
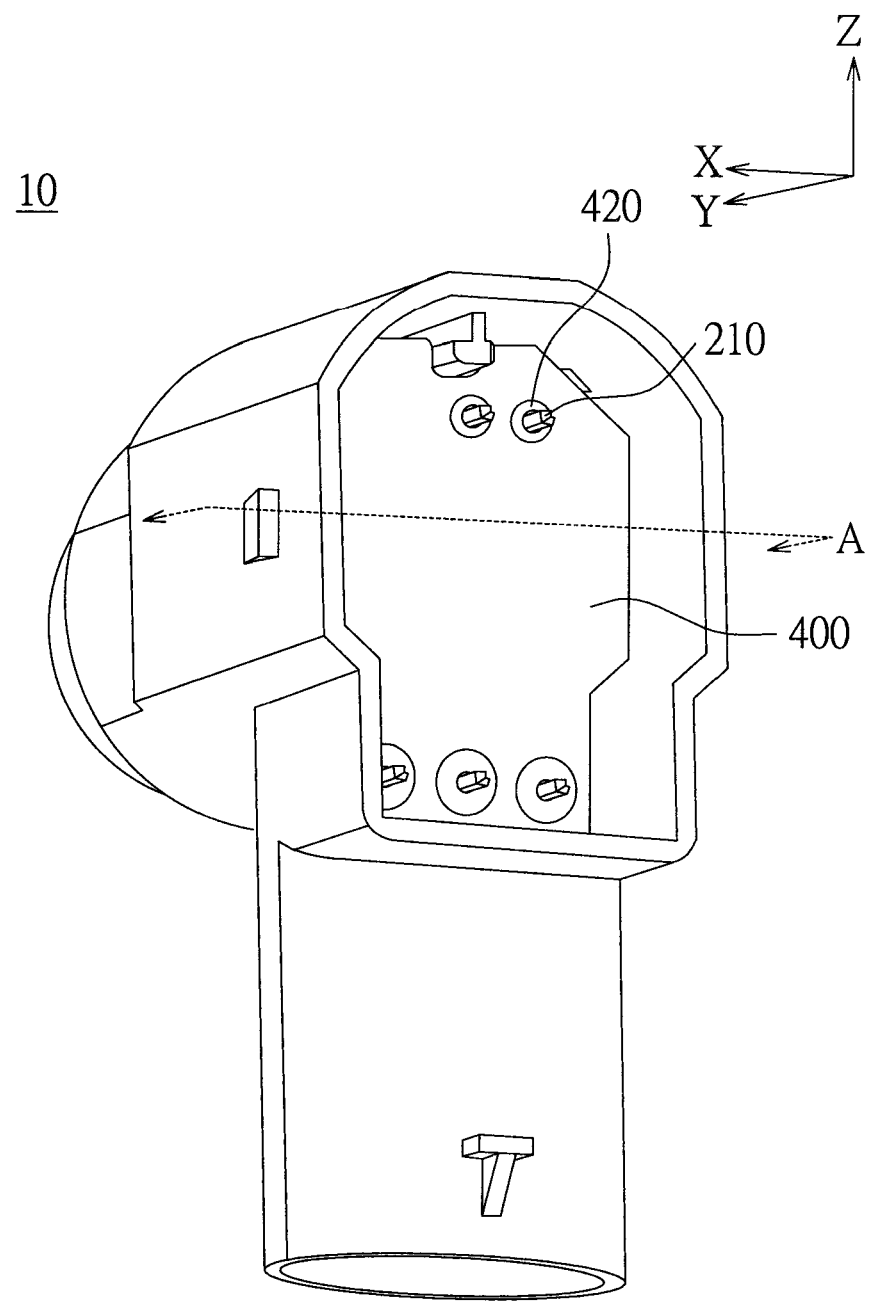
FIG. 3 shows a schematic view of the housing, the ultrasonic wave sensor and a circuit board assembled together, within the ultrasonic wave sensing module as shown in FIG. 1.

With reference to FIGS. 1 and 3, specifically, FIG. 3 shows a schematic view of the housing 100, the ultrasonic wave sensor 300 and the circuit board 400 that have been assembled, within the ultrasonic wave sensing module 10 as shown in FIG. 1. As described above, the second connecting portion 420 of the circuit board 400 can be an jack, and the second connecting pin 210 of the adapter 200 is inserted and welded into the jack. The circuit board 400 can includes other circuit elements like other connecting portions, connecting pins, jacks, or processors, so as to drive the ultrasonic wave sensing module 10.

Figure 4A:
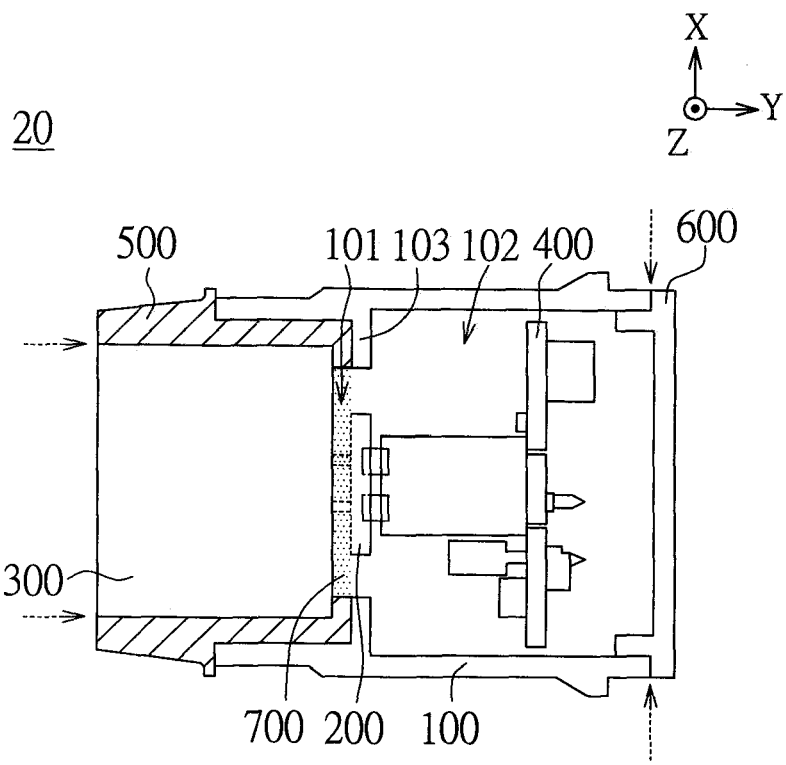
FIG. 4A shows a sectional view of the assembled ultrasonic wave sensing module in accordance with another embodiment of the present invention.

With reference to FIG. 4A, it shows a sectional view of the assembled ultrasonic wave sensing module in accordance with another embodiment of the present invention, the sectional direction of which substantially corresponds to a sectional line A of FIG. 3. The ultrasonic wave sensing module 20 of the present embodiment makes an improvement on the waterproof function. Since the remaining structures thereof are similar to those of the above ultrasonic wave sensing module 10, they are omitted herein.

As shown in FIG. 4A, the first containing space 101 of the ultrasonic wave sensing module 20 (in order to accommodate the ultrasonic wave sensor 300) is filled with waterproof glue 700. The waterproof glue 700 is for example polyurethane (PU) glue or other insulating glues for blocking the moisture, such as hot-melt adhesive made by low pressure molding. The waterproof glue 700 covers the connecting pin of the ultrasonic wave sensor 300, and blocks the opening holes in the blocking wall 103. In this way, the moisture entering from the ultrasonic wave sensor 300 (the dotted arrow indicates a path along which the moisture might enter) will be blocked by the waterproof glue 700, instead of contacting with the connecting pin or the circuit board, and thus short circuit caused by it may be avoided. In the present embodiment, the first containing space 101 is filled with the waterproof glue 700, but in other embodiments, the blocking wall 103 or the second containing space 102 may also be filled with it, so as to further block the moisture.

As shown in FIG. 4A, the second containing space 102 of the ultrasonic wave sensing module 20 is sealed by a sealing cover 600, which can prevent the moisture entering the second containing space 102 and resulting in the short circuit of the circuit board 400. The contacting portions of the sealing cover 600 with the housing 100 can be joined by means of ultrasonic wave welding or the like, so that the sealing cover 600 and the housing 100 become integral, and this prevents the moisture or dusts entering the second containing space 102 from the engagement thereof (along the dotted arrow). The designs of the sealing cover 600 and the waterproof glue 700 can reduce the contact area of the ultrasonic wave sensing module 20 with the external environment, and thus decrease the entering risk of the moisture or the dusts.

Figure 4B:
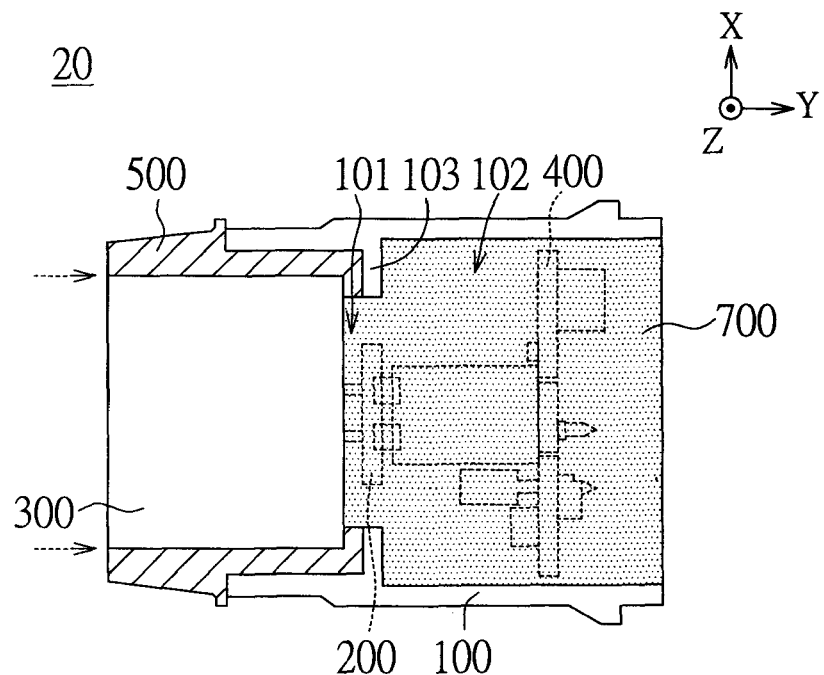
FIG. 4B shows a sectional view of the assembled ultrasonic wave sensing module in accordance with a yet another embodiment of the present invention.

With reference to FIG. 4B, it shows a sectional view of the assembled ultrasonic wave sensing module in accordance with a yet another embodiment of the present invention. The ultrasonic wave sensing module 30 is also designed to improve the waterproof thereof.

As shown in FIG. 4B, the first containing space 101, the second containing space 102 and the opening holes of the blocking wall 103 are filled with the waterproof glue 700. This figure shows the entire interior of the housing 100 filled up with the waterproof glue 700, but in practice, the blocking effect can be obtained as long as the waterproof glue 700 covers the circuit elements. In this circumstance, even if the moisture enters the housing 100, the short circuit in the ultrasonic wave sensor 300, the adapter 200 or the circuit board 400 would not occur.

With the ultrasonic wave sensing modules in accordance with the above embodiments, the adapter which is formed into the interior blocking wall of the housing by the insert molding, connects the ultrasonic wave sensor with the circuit board. This makes the circuit design of the circuit board to be more flexible, improves the shielding effect of the blocking wall, and simplifies the assembling process as well as reduces the costs of the parts. In addition, the containing spaces of the housing are sealed by the additionally provided sealing cover or waterproof glue, so that the waterproof and dustproof effects of the ultrasonic wave sensing module can be enhanced significantly. Therefore, it can normally function in various special working conditions.

Concerning the above, the embodiments of the present invention are disclosed as described above, but they are not intended to limit the present invention. The skilled person in the art having ordinary knowledge would make various variants and modifications, without departing from the sprits and scope of the present invention. Therefore, the protection scope of the present invention should be defined and delimited by the attached claims.

The invention claimed is:

1. A method of forming an ultrasonic wave sensing module for a vehicle, said method comprising:
   providing a housing having a first containing space and a second containing space separated from each other by a blocking wall;
   providing an adapter at the blocking wall, wherein the adapter comprises a first connecting portion and a second connecting portion, wherein the first connecting portion is electrically connected with the second connecting portion via an extension of the adapter;
   disposing an ultrasonic wave sensor in the first containing space so that a connecting pin of the ultrasonic wave sensor extends into the blocking wall;
   coupling the connecting pin of the ultrasonic wave sensor to the first connecting portion of the adapter at least partially between a first side surface and a second side surface of the blocking wall;
   disposing a circuit board in the second containing space, wherein the circuit board comprises an engaging portion;
   coupling the engaging portion of the circuit board to the second connecting portion of the adapter; and
   wherein, with the connecting pin of the ultrasonic wave sensor coupled to the first connecting portion of the adapter, and with the engaging portion of the circuit board coupled to the second connecting portion of the adapter, the ultrasonic wave sensor is electrically connected with the circuit board via the adapter.

2. The method of claim 1, wherein the first connecting portion of the adapter is disposed at least partially between opposite side surfaces of the blocking wall.

3. The method of claim 2, wherein coupling the connecting pin of the ultrasonic wave sensor to the first connecting portion of the adapter comprises coupling the connecting pin of the ultrasonic wave sensor to the first connecting portion of the adapter between the opposite side surfaces of the blocking wall.

4. The method of claim 1, wherein the first connecting portion and the second connecting portion of the adapter are electrically connected via an extension portion that locates the first connecting portion and the second connecting portion at different positions on the blocking wall, and wherein the extension portion is disposed at least partially between opposite side surfaces of the blocking wall.

5. The method of claim 1, further comprising disposing a rubber ring between the ultrasonic wave sensor and the first containing space.

6. The method of claim 1, further comprising dispensing adhesive to fill the first containing space for protecting the ultrasonic wave sensor from exposure to moisture.

7. The method of claim 1, further comprising dispensing adhesive to fill the second containing space for protecting the circuit board from exposure to moisture.

8. The method of claim 7, comprising coupling a sealing cover with the housing after the second containing space is filled with the adhesive.

9. The method of claim 1, wherein coupling the connecting pin of the ultrasonic wave sensor to the first connecting portion of the adapter comprises coupling the connecting pin of the ultrasonic wave sensor to the first connecting portion of the adapter via welding.

10. The method of claim 1, wherein coupling the engaging portion of the circuit board to the second connecting portion of the adapter comprises coupling the engaging portion of the circuit board to the second connecting portion of the adapter via welding.

11. The method of claim 1, wherein the blocking wall has at least one hole at the first connecting portion of the adapter, and wherein the connecting pin of the ultrasonic wave sensor extends through the hole to couple with the first connecting portion of the adapter.

12. The method of claim 1, wherein the first connecting portion and the second connecting portion are formed with the blocking wall via insert molding.

13. A method of forming an ultrasonic wave sensing module for a vehicle, said method comprising:
   providing a housing having a first containing space and a second containing space separated from each other by a blocking wall;
   providing an adapter at the blocking wall, wherein the adapter comprises a first connecting portion and a second connecting portion, wherein the first connecting portion is electrically connected with the second connecting portion via an extension of the adapter;
   wherein the first connecting portion and the second connecting portion of the adapter are electrically connected via an extension portion that locates the first connecting portion and the second connecting portion at different positions on the blocking wall, and wherein the first connecting portion and the extension portion are disposed at least partially between opposite side surfaces of the blocking wall;
   disposing an ultrasonic wave sensor in the first containing space so that a connecting pin of the ultrasonic wave sensor extends into the blocking wall;
   coupling the connecting pin of the ultrasonic wave sensor to the first connecting portion of the adapter at least partially between a first side surface and a second side surface of the blocking wall;
   disposing a circuit board in the second containing space, wherein the circuit board comprises an engaging portion;
   coupling the engaging portion of the circuit board to the second connecting portion of the adapter;
   wherein, with the connecting pin of the ultrasonic wave sensor coupled to the first connecting portion of the adapter, and with the engaging portion of the circuit board coupled to the second connecting portion of the adapter, the ultrasonic wave sensor is electrically connected with the circuit board via the adapter; and coupling a sealing cover with the housing to seal the second containing space.

14. The method of claim 13, wherein coupling the connecting pin of the ultrasonic wave sensor to the first connecting portion of the adapter comprises coupling the connecting pin of the ultrasonic wave sensor to the first connecting portion of the adapter between the opposite side surfaces of the blocking wall.

15. The method of claim 13, further comprising disposing a rubber ring between the ultrasonic wave sensor and the first containing space.

16. A method of forming an ultrasonic wave sensing module for a vehicle, said method comprising:
providing a housing having a first containing space and a second containing space separated from each other by a blocking wall;
providing an adapter at the blocking wall, wherein the adapter comprises a first connecting portion and a second connecting portion, wherein the first connecting portion is electrically connected with the second connecting portion via an extension of the adapter;
wherein providing the adapter comprises insert molding the first connecting portion and the second connecting portion with the blocking wall;
wherein providing the adapter comprises forming the blocking wall with at least one hole at the first connecting portion of the adapter;
disposing an ultrasonic wave sensor in the first containing space so that a connecting pin of the ultrasonic wave sensor extends into the blocking wall;
coupling the connecting pin of the ultrasonic wave sensor to the first connecting portion of the adapter at least partially between a first side surface and a second side surface of the blocking wall;
wherein coupling the connecting pin to the first connecting portion comprises inserting the connecting pin of the ultrasonic wave sensor into the at least one hole at the first connecting portion of the adapter;
disposing a circuit board in the second containing space, wherein the circuit board comprises an engaging portion;
coupling the engaging portion of the circuit board to the second connecting portion of the adapter; and
wherein, with the connecting pin of the ultrasonic wave sensor coupled to the first connecting portion of the adapter, and with the engaging portion of the circuit board coupled to the second connecting portion of the adapter, the ultrasonic wave sensor is electrically connected with the circuit board via the adapter.

17. The method of claim 16, wherein the first connecting portion of the adapter is disposed at least partially between opposite side surfaces of the blocking wall.

18. The method of claim 16, wherein the first connecting portion and the second connecting portion of the adapter are electrically connected via an extension portion that locates the first connecting portion and the second connecting portion at different positions on the blocking wall.

19. The method of claim 16, further comprising filling the first containing space with a filling material to protect the ultrasonic wave sensor from exposure to moisture.

20. The method of claim 16, further comprising filling the second containing space with a filling material to protect the circuit board from exposure to moisture.

* * * * *